(12) United States Patent
Murphy et al.

(10) Patent No.: US 8,968,797 B2
(45) Date of Patent: Mar. 3, 2015

(54) BIOACTIVE LOAD-BEARING COMPOSITES

(75) Inventors: James P. Murphy, Newtown Square, PA (US); Erik M. Erbe, Berwyn, PA (US); Charanpreet S. Bagga, Wayne, NJ (US); Marissa M. Darmoc, Philadephia, PA (US)

(73) Assignee: Orthovita, Inc., Malvern, PA (US)

( * ) Notice: Subject to any disclaimer, the term of this patent is extended or adjusted under 35 U.S.C. 154(b) by 740 days.

(21) Appl. No.: 12/442,531

(22) PCT Filed: Sep. 25, 2007

(86) PCT No.: PCT/US2007/020764
§ 371 (c)(1),
(2), (4) Date: Oct. 30, 2009

(87) PCT Pub. No.: WO2008/039488
PCT Pub. Date: Apr. 3, 2008

(65) Prior Publication Data
US 2010/0129416 A1 May 27, 2010

Related U.S. Application Data

(60) Provisional application No. 60/847,011, filed on Sep. 25, 2006.

(51) Int. Cl.
*A61K 33/14* (2006.01)
*A61K 33/06* (2006.01)
*A61K 33/42* (2006.01)
*A61F 2/28* (2006.01)
*A61L 27/44* (2006.01)

(52) U.S. Cl.
CPC .................................. *A61L 27/446* (2013.01)
USPC ........................... 424/722; 424/423; 424/602

(58) Field of Classification Search
None
See application file for complete search history.

(56) References Cited

U.S. PATENT DOCUMENTS

| | | | |
|---|---|---|---|
| 4,638,037 A | 1/1987 | Ward et al. | |
| 5,008,364 A | 4/1991 | Ittemann et al. | |
| 5,043,369 A | 8/1991 | Bahn et al. | |
| 5,074,916 A | 12/1991 | Hench et al. | |
| 5,336,465 A | 8/1994 | Matsunaga et al. | |
| 5,468,544 A | 11/1995 | Marcolongo et al. | |
| 5,645,934 A | 7/1997 | Marcolongo et al. | |
| 5,681,872 A * | 10/1997 | Erbe | 523/114 |
| 5,721,049 A | 2/1998 | Marcolongo et al. | |
| 5,914,356 A | 6/1999 | Erbe | |
| 6,121,172 A | 9/2000 | Marcolongo et al. | |
| 6,270,347 B1 | 8/2001 | Webster et al. | |
| 6,399,693 B1 | 6/2002 | Brennan et al. | |
| 6,602,293 B1 * | 8/2003 | Biermann et al. | 623/23.5 |
| 6,800,245 B1 | 10/2004 | Erbe et al. | |
| 6,808,908 B2 | 10/2004 | Yao et al. | |
| 6,979,702 B1 | 12/2005 | Ma et al. | |
| 6,987,136 B2 | 1/2006 | Erbe et al. | |
| 7,189,409 B2 | 3/2007 | Pirhonen et al. | |
| D539,934 S | 4/2007 | Blain | |
| D541,940 S | 5/2007 | Blain | |
| 7,230,039 B2 | 6/2007 | Trieu et al. | |
| 7,238,203 B2 | 7/2007 | Bagga et al. | |
| 7,241,486 B2 | 7/2007 | Pirhonen | |
| D564,095 S | 3/2008 | Blain | |
| D566,276 S | 4/2008 | Blain | |
| 2001/0043940 A1 | 11/2001 | Boyce et al. | |
| 2002/0115742 A1 | 8/2002 | Trieu et al. | |
| 2003/0031698 A1 | 2/2003 | Roeder et al. | |
| 2003/0087984 A1 * | 5/2003 | Erbe et al. | 523/113 |
| 2003/0100086 A1 | 5/2003 | Yao et al. | |
| 2003/0125739 A1 | 7/2003 | Bagga et al. | |
| 2003/0206928 A1 | 11/2003 | Tormala et al. | |
| 2003/0232122 A1 | 12/2003 | Chappa et al. | |
| 2004/0009228 A1 | 1/2004 | Tormala et al. | |
| 2005/0177238 A1 | 8/2005 | Khandkar et al. | |
| 2005/0283255 A1 | 12/2005 | Geremakis et al. | |
| 2006/0015184 A1 | 1/2006 | Winterbottom et al. | |
| 2006/0063882 A1 | 3/2006 | Velev et al. | |
| 2006/0172877 A1 | 8/2006 | Fechner et al. | |
| 2007/0293948 A1 | 12/2007 | Bagga et al. | |
| 2008/0234532 A1 | 9/2008 | De Langen et al. | |
| 2009/0164023 A1 | 6/2009 | Devine | |
| 2009/0288831 A1 | 11/2009 | Williams et al. | |

FOREIGN PATENT DOCUMENTS

| | | |
|---|---|---|
| EP | 0 055 472 | 11/1985 |
| EP | 0 125 816 | 9/1987 |
| EP | 0 148 633 | 5/1989 |
| EP | 0365236 A1 | 4/1990 |
| EP | 2 243 500 | 10/2010 |
| JP | 02-225343 A | 9/1990 |

(Continued)

OTHER PUBLICATIONS

Green, Stuart and Schlegel, Jorg; A polyaryletherketone biomaterial for use in medical implant application, Polymers for The Medical Industry (2001) Victrex plc, UK and Victrex Europa GmbH, Germany.
Converse and Roeder, "Hydroxyapatite Wisker Reinforced Polyetheretherketone: A Bone Mimetic Composite;" $52^{nd}$ Annual Meeting of the Orthopaedic Research Society; Mar. 19-22, 2006; Paper 0886 (2 pages).
Kim et al., "Bioactive Composites Consisting of PEEK and Calcium Silicate Powders" Journal of Biomaterials Applications, Aug. 29, 2008, vol. 00; pp. 1-14.
Von Wilmowsky et al., "Effects of bioactive glass and beta-TCP containing three dimensional laser sintered polyetheretherketone composites on osteoblasts in vitro." Wiley InterScience; Jan. 28, 2008; pp. 1-7.
Converse and Roeder; Hydroxyapatite Whisker Reinforced Polyetheretherketone: A Bone Mimetic Composite; 52nd Annual Meeting of the Orthopaedic Research Society; Mar. 19-22, 2006; Paper No. 0886; 2 pgs.

(Continued)

*Primary Examiner* — H. Sarah Park
(74) *Attorney, Agent, or Firm* — Lerner, David, Littenberg, Krumholz & Mentlik, LLP

(57) ABSTRACT

Methods of preparing bioactive composites are described. Also described are methods of molding such composites. Shaped bodies comprising bioactive composites are further described.

16 Claims, 12 Drawing Sheets

(56) References Cited

FOREIGN PATENT DOCUMENTS

| JP | 09-505345 A | 5/1997 |
|----|-------------|--------|
| JP | 2000515171 A | 11/2000 |
| JP | 2004521685 A | 7/2004 |
| JP | 2005511110 A | 4/2005 |
| JP | 2005520629 A | 7/2005 |
| JP | 2005535367 A | 11/2005 |
| WO | 9514127 A1 | 5/1995 |
| WO | WO99/36368 | 7/1999 |
| WO | WO 03/105919 | 12/2003 |
| WO | WO2008/039488 | 4/2008 |
| WO | 2010/007424 A1 | 1/2010 |
| WO | 2010/043900 A1 | 4/2010 |

OTHER PUBLICATIONS

Kim et al.; Bioactive Composites Consisting of PEEK and Calcium Silicate Powders; Journal of Biomaterials Applications, Aug. 29, 2008; vol. 00; pp. 1-14.
Wilmowsky et al.; Effects of bioactive glass and B-TCP containing three-dimensional laser sintered polyetheretherketone composites on osteoblasts in vitro; Wiley InterScience; Jan. 28, 2008; pp. 1-7.
Sagomonyants, K.B. et al, The In vitro response of human osteoblasts to polyetheretherketone (PEEK) substrates . . . pure titanium, Biomatl 29(2008)1563-1572 Elsevier Ltd.
International Search Report for PCT/US07/20764 dated Mar. 25, 2008.
Australian Office Action for Application No. 2007300509 dated May 29, 2012.
Extended European Search Report for Application No. EP07861377.5 dated Oct. 11, 2012.
Japanese Office Action for Application No. 2009-529275 dated Aug. 10, 2012.
Supplementary European Search Report for Application No. EP07861377 dated Oct. 2, 2012.
Japanese Office Action for Application No. 2009-529275 dated Jan. 10, 2013.
Bakar, M.S. A. et al; Tensile properties, tension-tension fatigue and biological response of polyetheretherketone-hydroxyapatite composites for load-bearing orthopedic implants; Biomaterials 24 (2003) pp. 2245-2250, Elsevier Sci Ltd.
Barton, A.J. et al; Bacterial adhesion to orthopedic implants polymers, Journal of Biomedical Materials Research, vol. 30, pp. 403-410 (1996) John Wiley & Sons, Inc.
Bureau, MN; et al; CaP coating on PEEK varies upon processing conditions, Industrial Materials Institute, National Research Council Canada, 55th Annual Meeting of the Orthopeadic Research Society, Poster No. 470 (date published??).
Converse and Roeder; Hydroxyapatite Wisker Reinforced Polyetheretherketone: A Bone Mimetic Composite; 52nd Annual Meeting of the Orthopaedic Research Society; Mar. 19-22, 2006; Paper 0886; 2 pgs.
Converse, G. L et al; Processing and tensile properties of hydroxyapatite-whisker-reinforced polyetheretherketone; Biomaterials 28 (2007), pp. 927-935 Elsevier Ltd.
Extended European Search Report for Application No. EP09866889 dated Dec. 3, 2013.
International Search Report of PCT/US09/68257 dated Feb. 23, 2010.
Jones, D.P. et al; Mechanical properties of poly(ether-ether-ketone) for engineering applications; Mechanical properties of PEEK; Polymer, 1985, vol. 26, pp. 1385-1393, Aug. (Conference issue), Butterworth & Co.
Kim et al; Bioactive Composites Consisting of PEEK and Calcium Silicate Powders; Journal of Biomaterials Applications, Aug. 29, 2008; vol. 00; pp. 1-14 Beta-TCP containing three-dimensional laser sintered polyetheretherketone composites on oseoblasts in vitro.
Kurtz, S.M. and Devine, J.N.; PEEK biomaterials in trauma, orthopedic, and spinal implants; Biomaterials 28 (2007), D pp. 4845-4869, Elsevier Ltd.
Lin, T.W. et al; Glass peek composite promotes proliferation and osteocalcin production of human osteoblastic cells,11 Student Research Award in the Undergraduate, Master, Candidate, or Health Science Degree Candidate Category, Society for Biomaterials 23rd Annual Meeting, New Orleans, LA, Apr. 30-May 4, 2007; John Wiley & Sons, Inc.
Inagaki N. et al; Surface modification of poly(aryl ether ether ketone) film by remote oxygen plasma; Journal of Applied Polymer Science, vol. 68, pp. 271-279 (1998) John Wiley & Sons, Inc.
Pino, M., et al; Nucleation and growth of apatite on NaOH-treated PEEK, HDPE, and UHMWPE for artificial cornea materials; Acta Biomaterials 4 (2008) pp. 1827-1836, Elsevier Ltd.
Rivard C.H., et al.; In vivo biocompatibility testing of peek polymer for a spinal implant system: A study in rabbits; Peek Biocompatibility for a Spinal Implant, J. Biomed Mater Res 62: 488-498, 2002 Wiley Periodicals, Inc.
Sagomonyants, K.B. et al; The in vitro response of human osteoblasts to polyetheretherketone (PEEK) substrates compared to commercially pure titanium; Biomaterials 29 (2008) pp. 1563-1572, Elsevier Ltd.
von Wilmonsky et al; Effects of bioactive glass and Beta-TCP containing three-dimensional laser sintered polyetheretherketone composites or osteoblasts in vitro; Wiley InterScience; Jan. 28, 2008; pp. 1-7.
Wang, Min; Developing bioactive composite materials for tissue replacement; Biomaterials 24 (2003) pp. 2133-2151, Elsevier Ltd.
Wong, K.L. et al; Mechanical properties and in vitro response of strontium-containing hydroxyapatite/polyetheretherkone composites; Biomaterials 30 (2009) 3810-3817, Elsevier Ltd.
Baker, M.S. et al; Tensile properties, tension-tension fatigue and biological response of polyetheretherketone-hydroxyapatite composites for load-bearing orthopedic implants; Biomaterials 24(2003) pp. 2245-2250, Elvsevier Sci Ltd. 11111.
Barton, A.J. et al; Bacterial adhesion to orthopedic implants polymers, Journal of Biomaterial Materials Research, vol. 30 pp. 403-410 (1996) John Wiley & Sons, Inc.
Converse, G.L. et al; Processing and tensile properties of hydroxyapatite-whisker-reinforced polyetheretherketone; Biomaterials 28(2007), pp. 927-935 Elvsevier Ltd.
Fan, J.P, et al; Influence of interphase layer on the overall elasto-plastic behaviors of HA/PEEK biocomposite, Biomaterials 25 (2004), pp. 5363-5373, Elsevier Ltd.
Inagaki N. et al; Surface modification of poly(aryl ether ether ketone) film by remote oxygen plasma; Journal of Applied Polymer Science. vol. 68, pp. 271-279 (1998) John Wiley & Sons, Inc.
Jones, D.P. et al; Mechanical properties of poly(ether ether ketone) for engineering applications; Mechanical properties of PEEK: Polymer, 1985, vol. 26, pp. 1385-1393, Aug. (Conference issue), Butterworth & Co.
Kurtz, S.M. and Devine, J.N.; PEEK biomaterials in trauma, orthopedic, and spinal implants; Biomaterials 28(2007), pp. 4845-4869, Elsevier Ltd.
Lin, T.W. et al; Glass peek composite promotes proliferation and osteocalcin production of osteoblastic cells, Student Research Award in the Undergraduate, Master, Candidate, or Health Science Degree Candidate Category, Society for Biomaterials 23rd Annual Meeting, New Orleans, LA, Apr. 30-May 4, 2007; John Wiley & Sons, Inc.
Pino, M. et al; Nucleation and growth of apatite on NaOH-treated PEEK, HDPE, and UHMWPE for artifical cornea materials; Acta Biomaterials 4 (2008) pp. 1827-1836, Elsevier Ltd.
Rivard C.H., et al.; In vivo biocompatibility testing of peek polymer for a spinal implant system: A study in rabbits; PEEK Biocompatibility for a Spinal Implant, J. Biomed Mater Res. 62: 488-498, 2002 Wiley Periodicals, Inc.
Tang S.M et al; Tension-Tension fatigue behavior of hydroxyapatite reinforced polyetheretherketone composites International Journal of Fatigue 26 (2004) pp. 49-57, Elsevier Ltd.
Wang, Min; Developing Bioactive composite materials for tissue replacement; Biomaterials 24 (2003) pp. 2133-2151 Elsevier Ltd.
Bureau, MN et al; CaP coating on PEEK varies upon processing conditions, Industrial Materials Institute, National Research Council Canada, 55th Annual Meeting of the Orthopeadic Research Society, Poster No. 470, (2009).

(56) References Cited

OTHER PUBLICATIONS

Chou, Yu-Cheng et al; Efficacy of anterior cervical fusion: Comparison of titanium cages, polyetheretherketone (PEEK) cages and autogenous bone grafts; Journal of Clinical Neuroscience 15 (2008) 1240-1245.

Jiya, Timothy et al; Posterior lumbar interbody fusion using nonresorbable poly-ether-ether-ketone versus resorbable poly-L-Lactide-Co-D, L-Lactide Fusion Devices; SPINE vol. 23 No. 3 pp. 233-237 (2009) Lippincott Williams & Wilkins.

Green Stuart and Shlegel, Jorg; A polyaryletherketone biomaterial fro use in medical implant application, Polymers for the Medical Industry (2001) Victrex plc, UK and Victrex Europa GmbH, Germany.

* cited by examiner

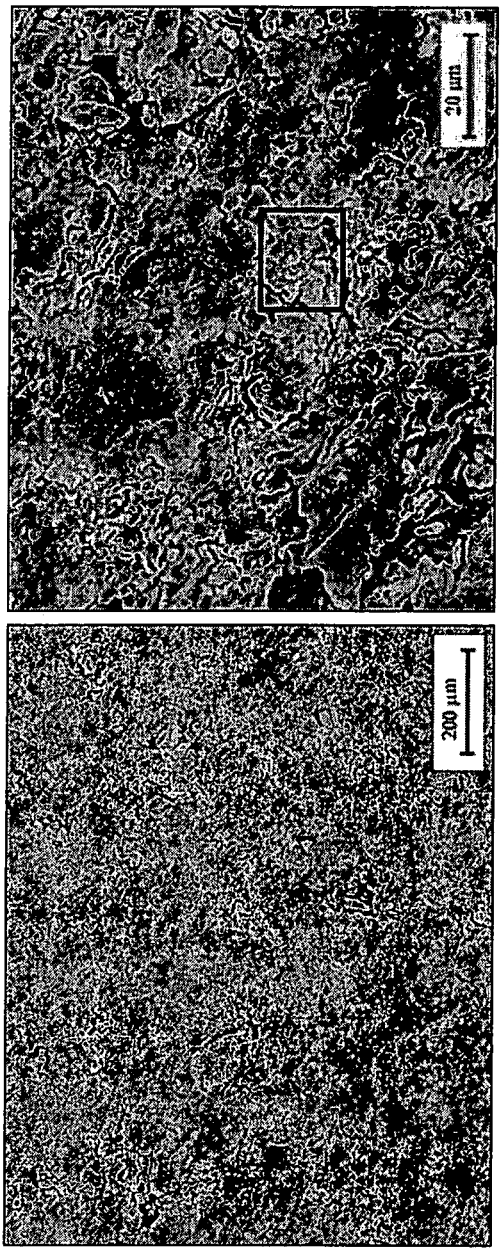
FIG 2A
FIG 2B
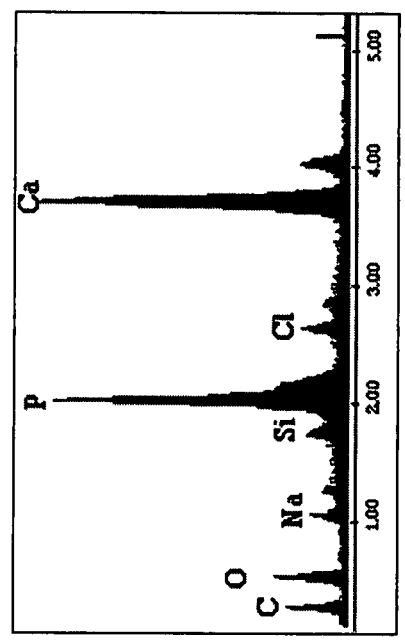
FIG 2C

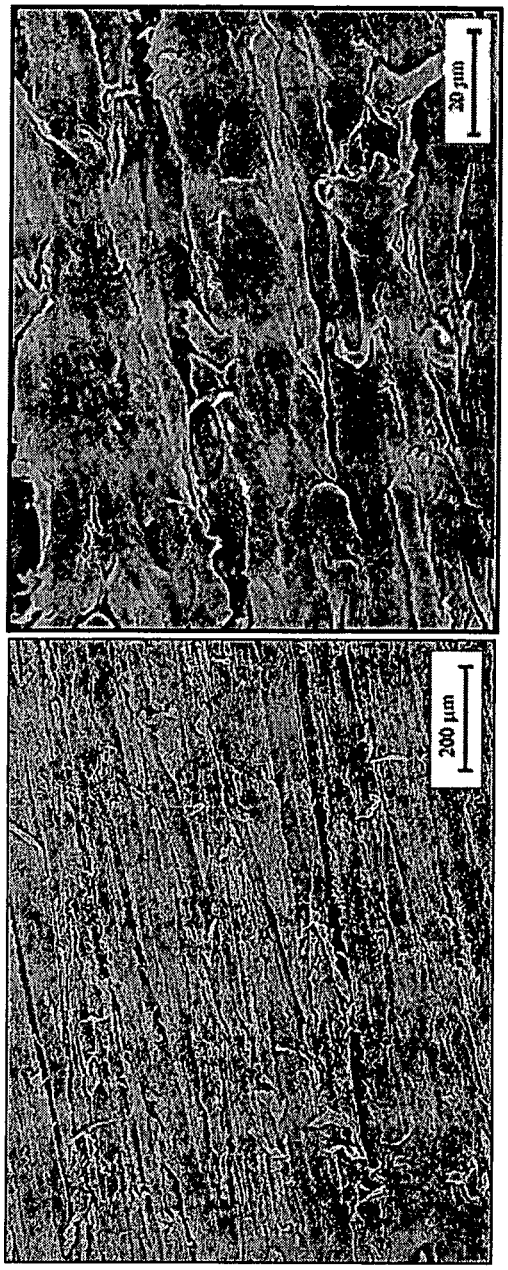
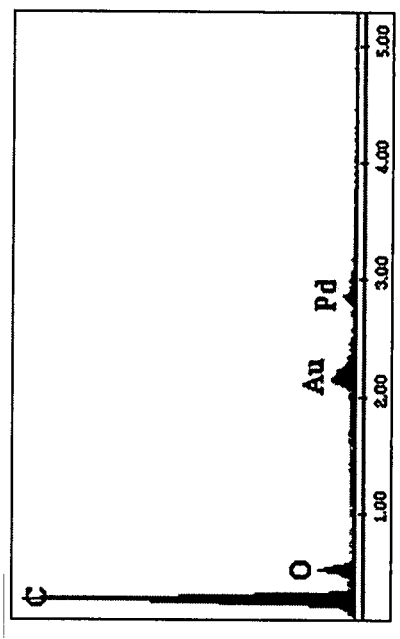
FIG 3B
FIG 3A
FIG 3C

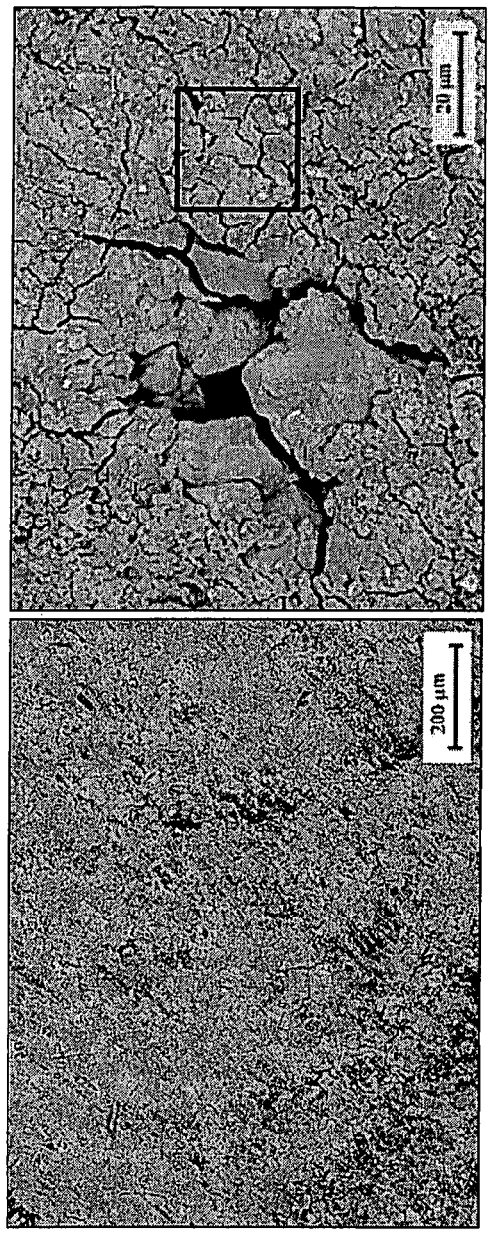
FIG 4A
FIG 4B
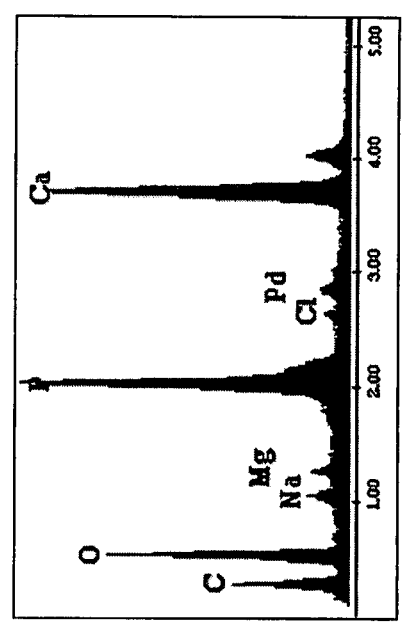
FIG 4C

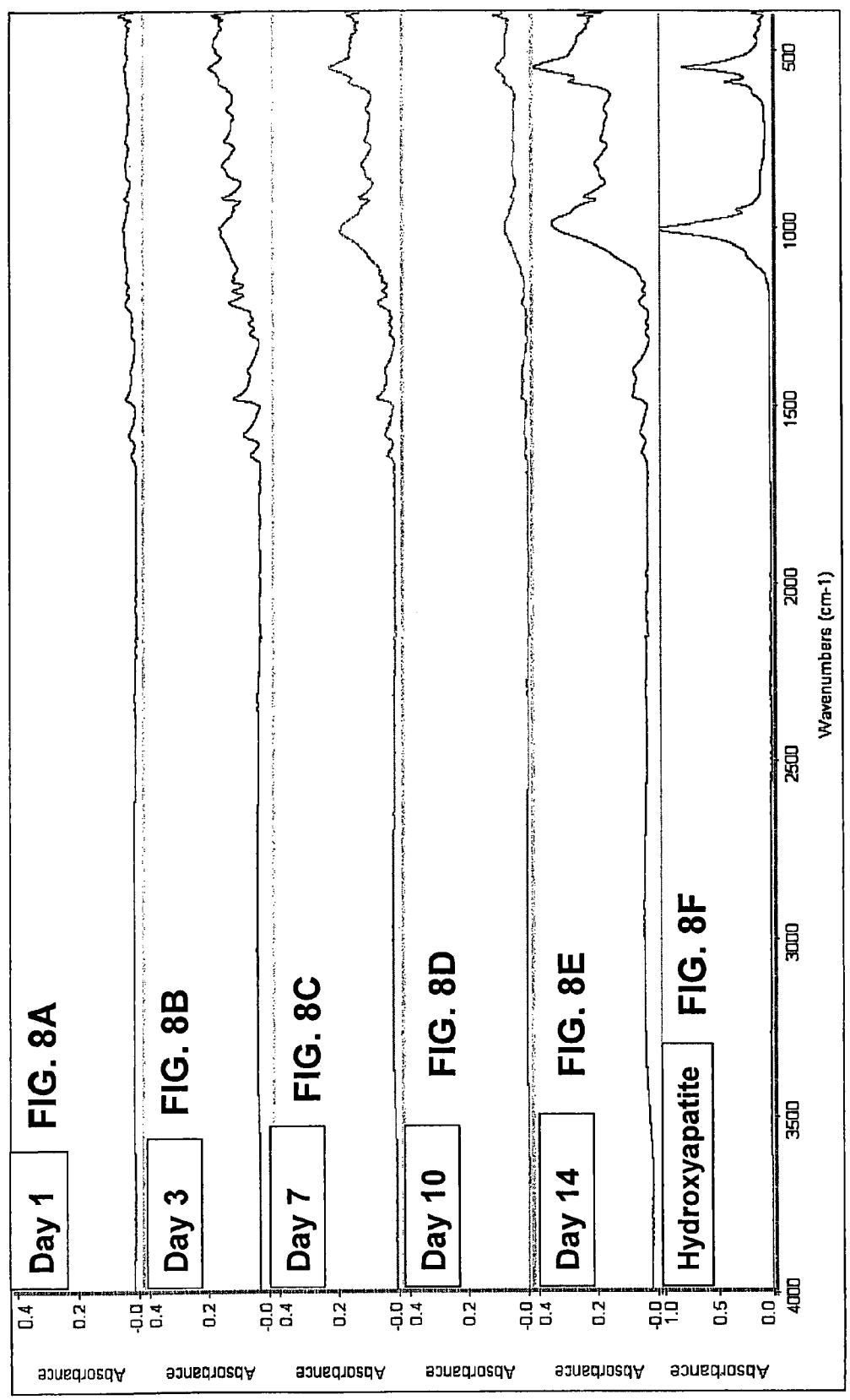

BIOACTIVE LOAD-BEARING COMPOSITES

CROSS-REFERENCE TO RELATED APPLICATIONS

This application claims the benefit of priority to U.S. Provisional Patent Application Ser. No. 60/847,011, filed Sep. 25, 2006, which is herein incorporated by reference in its entirety.

FIELD OF THE INVENTION

This invention relates to the preparation of bioactive composites comprising a polymer and a bioactive glass ceramic. The invention further relates to the use of these composites in the preparation of biocompatible implantable materials and integral shaped bodies.

BACKGROUND OF THE INVENTION

Lower back pain may oftentimes be attributed to the rupture or degeneration of lumbar intervertebral discs due to degenerative disk disease, isthmic spondylolisthesis, post laminectomy syndrome, deformative disorders, trauma, tumors and the like. This pain may result from the compression of spinal nerve roots by damaged discs between the vertebra, the collapse of the disc, and the resulting adverse effects of bearing the majority of the patient's body weight through a damaged unstable vertebral joint. To remedy this, spinal implants may be inserted between the vertebral bodies to restore the joint to its previous height and stabilize the motion at that spinal segment.

Numerous materials have been described for the preparation of spinal implants that possess desired mechanical and biological properties. Polyetheretherketone (PEEK) is a thermoplastic with excellent mechanical properties, including a Young's modulus of about 3.6 GPa and a tensile strength of about 100 MPa. PEEK is partially crystalline, melts at about 334° C., and is resistant to thermal degradation. PEEK is a biomaterial used in medical implants. For example, PEEK can be molded into preselected shapes that possess desirable load-bearing properties. But such materials are not bioactive, osteoproductive, or osteoconductive. Bioactive glasses and glass-ceramics are characterized by their ability to form a direct bond with bone. A material based on the PEEK polymer, or similar types of polymers of the PEEK family that includes the bone-bonding properties of a bioactive glass would be desirable.

The prior art does not provide a material or a method of making the material which combines a biocompatible polymer such as PEEK with a bioactive glass having a particle size larger than one micron. Furthermore, the art does not disclose a material or method of making a bioactive implant material which combines PEEK and bioactive glass and which has the appropriate structural and mechanical properties to withstand the stresses necessary for use in spinal implants.

A combination of polymers including PEEK and combeite glass-ceramic, a bioactive glass, has generally been described in U.S. Pat. Nos. 5,681,872; 5,914,356; and 6,987,136; each of which is assigned to the assignee of the present invention and is incorporated herein by reference in its entirety. It has been discovered, however, that conventional methods of combining PEEK and combeite, for example, combination using a twin screw extruder, result in a reaction between the PEEK and the combeite glass-ceramic forming a material having properties that inhibit extruder functioning. In some instances, the high reactivity of such bioactive materials with the polymers makes combining bioactive materials, such as glass, ceramics, and glass-ceramics, with PEEK, or similar polymers of the PEEK family, a challenge using conventional processing. What is needed, therefore, is a method of preparing a composite of PEEK and bioactive glass.

SUMMARY OF THE INVENTION

The present invention is directed to methods of preparing bioactive composites formed of particles of both polyetheretherketone (PEEK) and bioactive glass. Provided herein are novel methods which blend such particles together and then add to the blend a polar organic solvent, such as alcohol. The preferred ethyl alcohol is present when the blend is agitated by sonication, vibration or other methodologies to achieve substantial homogeneity of the blend. The solvent is then removed, such as in vacuo, to yield a homogeneous blend of particles ready for formation of composite shaped bodies useful for orthopedics, such as in the preparation of spinal implants.

Control of particle sizes is preferred. Average particle sizes of from about 1 to about 200 microns, especially of from about 10 to about 25 microns, are preferred for the bioactive glass. Combeite glass-ceramic is a preferred bioactive glass for these purposes. Amounts of bioactive glass particles of from about 5 to about 60% by weight of the particle mixture are preferred with amounts of from about 45 to about 55% being more preferred. For some embodiments, PEEK particles in the same or greater quantities by number than the bioactive glass are preferred with number ratios of from about 6:1 to about 10:1 being preferred. Additional materials, such as fillers, including reinforcing fibers, may also be included.

It is preferred that the particle blend mixed with polar organic solvent contains little or no water. Less than 5% by weight of water (in the solvent) is preferred with less than 1% being more preferred. Solvent to particle weight ratios of 2:1 to 10:1 are preferred. Preferred solvents are alcohols, with the medically acceptable ethanol being more preferred.

After removal of solvent, the blend of PEEK and bioactive glass particles is substantially homogeneous and ready for molding or other the formation of other shaped bodies. Application of conditions of temperature and pressure for appropriate times gives molded, shaped bodies useful for orthopaedic, especially spinal, use. Further shaping such as by machining may be performed.

The present invention is also drawn to the shaped bodies and implants provided herein. Persons of skill in the art will appreciate that the conditions of temperature, pressure, and time will generally be dependent variables whose determination will require only routine experimentation for any particular blend of particles and for any particular object to be formed. Determining such conditions to effect fusing of the PEEK particles to form the shaped bodies is well within the ordinary skill of those in the molding art.

BRIEF DESCRIPTION OF THE DRAWINGS

FIG. 2A depicts a SEM (100×) of an exemplary embodiment of the present invention comprising PEEK and combeite glass-ceramic (50% by weight), after immersion in SBF for 1 day.

FIG. 2B depicts a SEM (1000×) of an exemplary embodiment of the present invention comprising PEEK and combeite glass-ceramic (50% by weight), after immersion in SBF for 1 day.

FIG. 2C depicts an EDS spectrum of an exemplary embodiment of the present invention comprising PEEK and combeite glass-ceramic (50% by weight), after immersion in SBF for 1 day. The spectrum corresponds to the boxed area of FIG. 2B.

FIG. 3A depicts a SEM (100×) of a sample of PEEK after immersion in simulated body fluid (SBF) for 7 days.

FIG. 3B depicts a SEM (1000×) of a sample of PEEK after immersion in SBF for 7 days.

FIG. 3C depicts an EDS spectrum of a sample of PEEK after immersion in SBF for 7 days. The spectrum corresponds to the sample region shown in FIG. 3B.

FIG. 4A depicts a SEM (100×) of an exemplary embodiment of the present invention comprising PEEK and combeite glass-ceramic (50% by weight), after immersion in SBF for 7 days.

FIG. 4B depicts a SEM (1000×) of an exemplary embodiment of the present invention comprising PEEK and combeite glass-ceramic (50% by weight), after immersion in SBF for 7 days.

FIG. 4C depicts an EDS spectrum of an exemplary embodiment of the present invention comprising PEEK and combeite glass-ceramic (50% by weight), after immersion in SBF for 7 days. The spectrum corresponds to the boxed area of FIG. 4B.

FIGS. 8A-8E depict FTIR spectra of an exemplary embodiment of the present invention comprising PEEK and combeite glass-ceramic (50% by weight). FIG. 8A is an FTIR spectra taken after 1 day of immersion in SBF. FIG. 8B is an FTIR spectra taken after 3 days of immersion in SBF. FIG. 8C is an FTIR spectra taken after 7 days of immersion in SBF. FIG. 8D is an FTIR spectra taken after 10 days of immersion in SBF. FIG. 8E is an FTIR spectra taken after 14 days of immersion in SBF.

FIG. 8F is an FTIR spectrum of hydroxyapatite.

FIG. 10A is a representation of a cross-section of homogeneous composite structure wherein the bioactive filler particles are roughly evenly distributed throughout the composite. FIG. 10B is a representation of a cross-section of a gradient composite structure wherein the bioactive filler particles are concentrated toward the surface of the composite and diminish toward the interior of the composite. FIG. 10C is a representation of a cross-section of a composite structure with surface adhered bioactive layers.

DETAILED DESCRIPTION OF ILLUSTRATIVE EMBODIMENTS

Figure 1B:
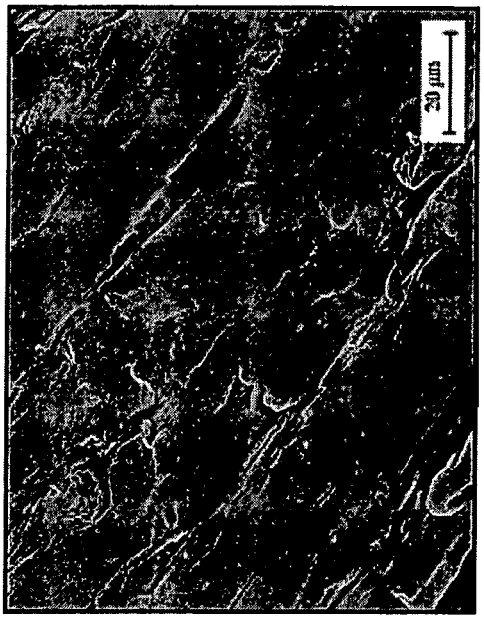
FIG. 1B depicts a SEM (1000×) of a sample of PEEK after immersion in SBF for 1 day.

According to the present invention, methods for preparing bioactive molding composites comprising polyetheretherketone (PEEK), or similar types of polymers in this family, and bioactive glass are described. Also described are methods of preparing bioactive implants comprising PEEK and bioactive glass, as well as shaped bodies for intercorporeal implantation that comprise PEEK and bioactive glass.

Preferably, medical grade PEEK is used in the present invention, although industrial-grade PEEK can also be incorporated. PEEK is available as a powder and a desirable PEEK material for use in the present invention has an average particle size of about 1 to about 200 microns. PEEK material having an average particle size of about 1 to about 400 microns is also suitable. Preferably, the PEEK material has an average particle size of about 10 to about 100 microns.

The bioactive glass used in the present invention may be any alkali-containing ceramic (glass, glass-ceramic, or crystalline) material that reacts as it comes in contact with physiological fluids including, but not limited to, blood and serum, which leads to bone formation. In preferred embodiments, bioactive glasses, when placed in physiologic fluids, form an apatite layer on their surface.

Preferably, the bioactive glass comprises at least one alkali metal, for example, lithium, sodium, potassium, rubidium, cesium, francium, or combinations thereof. In a preferred embodiment, the bioactive glass comprises regions of combeite crystallite morphology. Such bioactive glass is referred to herein as "combeite glass-ceramic". Examples of preferred bioactive glasses suitable for use in the present invention are described in U.S. Pat. Nos. 5,914,356 and 5,681,872, each of which is incorporated by reference herein in its entirety. Other suitable bioactive materials include 45S5 glass and compositions comprising calcium-phosphorous-sodium silicate and calcium-phosphorous silicate. Further bioactive glass compositions that may be suitable for use in the present invention are described in U.S. Pat. No. 6,709,744, incorporated herein by reference. Other suitable bioactive glasses include borosilicate, silica, and Wollastonite. Suitable bioactive glasses include, but are not limited to, silica-, borate-, and phosphate-containing materials. It is understood that some non-alkali-containing bioactive glass materials are within the spirit of the invention. Bioactive glasses, as defined herein, do not include calcium phosphate materials, for example, hydroxyapatite and tri-calcium phosphate.

In exemplary embodiments of the present invention, the bioactive glass possesses osteoproductive properties. As used herein, "osteoproductive" refers to an ability to allow osteoblasts to proliferate, allowing bone to regenerate. Osteoproductive may also be defined as conducive to a process whereby a bioactive surface is colonized by osteogenic stem cells and which results in more rapid filling of defects than that produced by merely osteoconductive materials. Combeite glass-ceramic is an example of an osteoproductive material.

Preferably, the bioactive glass has an average particle size of about 1 to about 400 microns. Bioactive glass may have an average particle size of about 1 to about 200 microns, about 1 to about 100 microns, or about 10 to about 100 microns. More preferably, the bioactive glass has an average particle size of about 5 to about 40 microns. Most preferred are bioactive glasses having an average particle size of about 10 to about 25 microns. In some embodiments, the bioactive glass has an average particle size of less than or about 53 microns. It is envisioned that in certain embodiments of the present invention, the bioactive particles are nanoparticulate. In some embodiments, nanoparticulate bioactive glass is substantially excluded. In some embodiments, the bioactive glass has average particle sizes larger than about 500 nm. It is also contemplated that a blend of bioactive particles of differing average particle sizes may be employed.

Methods of determining particle sizes are known in the art. Some methods include passing the particles through several sieves to determine general particle size ranges. Other methods include laser light scattering, and still others are known to persons skilled in the art. Determination of particle size is conveniently accomplished by sieving and such may be used here. Particle size may also be appreciated via SEM image analysis. It will be appreciated that recitation of averages or size ranges is not meant to exclude every particle with a slightly higher or lower dimension. Rather, sizes of particles are defined practically and in the context of this invention.

According to the present invention, PEEK particles and bioactive glass particles are blended to form a particle mixture. The blending of the bioactive component with PEEK particles may be accomplished using any methods known in the art per se, including mixing, milling, spinning, tumbling, vibrating, or shaking. In certain embodiments, the bioactive glass is present in an amount of about 5-60% by weight of the particle mixture. In other embodiments, the bioactive glass is present in an amount of about 45-55% by weight of the particle mixture. In other embodiments, the bioactive glass is present in an amount of about 50% by weight of the particle mixture. In certain variations of the present invention, the number of PEEK particles is greater than the number of bioactive glass particles. In other variations, the ratio of PEEK particles to bioactive glass particles is between about 6:1 and about 10:1, inclusive. In certain preferred embodiments, the particle size ratio of PEEK particles to bioactive glass particles is about 1:1.5.

While not desiring to be bound to any particular theory, it is believed that the combination of PEEK and bioactive glass using conventional methods is inhibited due to the reactivity of the surface of the bioactive glass with PEEK. In such situations, it may be desirable to prepare the bioactive component prior to its combination with PEEK, or similar polymers. In one embodiment, preparation of the bioactive component may comprise treatment with an agent which serves to remove at least a portion of reactive alkali which may be present at the surface of the bioactive particle component. Aqueous solutions, such as those containing a mildly acidulating agent, may be employed for this purpose. In another embodiment, the bioactive particles can be coated with PEEK or other polymers compatible with PEEK. In yet another embodiment, at least a portion of the surface alkali of the bioactive component may be depleted, leached, or washed, such that the surface alkali is minimized. Such minimization can be achieved by coating, flame spheroidization, or chemical treatment. It is understood that such surface treatments serve to reduce reactivity at the surface of the bioactive component. In one embodiment, the reactive constituent, such as alkali, for example, is reduced at the surface of the bioactive component and up to about 5 to about 10 microns into the bioactive component. Such bioactive components retain bioactivity.

In certain embodiments of the present invention, the bioactive glass particles and polymer (for example, PEEK) particles may be prepared prior to their combination. For example, the bioactive glass particles may be prepared by rinsing, adjusting particle size, spheroidizing, coating, and/or chemically treating. The polymer (for example, PEEK) particles may be prepared by determining particle size, particle size distribution, composition, molecular weight, purity, viscosity, and/or particle shape. In certain embodiments, the combination of the prepared bioactive glass particles and the polymer (for example, PEEK) particles may be achieved by blending. Blending sufficient to obtain substantial homogeneity of the mixture may be accomplished using techniques known in the art, for example, sonicating, rolling, milling, impact milling, and/or a chemical slurry. In certain embodiments, the blending may be sufficient to provide a composite having a gradient of bioactive material. In others, the blending may be sufficient to provide a composite having at least one layer of bioactive material. In yet others, the blending may be sufficient to form a coating. According to the present invention, the blended material may be fused. Such fusion may be accomplished using techniques known in the art, including molding, compacting, and/or pressure molding. Thus, provided herein is a method of preparing a bioactive composite article comprising preparing bioactive glass particles, preparing PEEK particles, blending the PEEK particles with the bioactive glass particles to form a particle mixture, and fusing the mixture to form the article.

In the present invention, a polar organic solvent is added to the particle mixture. Preferably, the weight ratio of solvent to particle mixture is about 1:1 to about 4:1. Most preferably, the weight ratio of solvent to particle mixture is about 2:1. Certain preferred solvents include alcohols, for example ethanol, methanol, and isopropanol. Other solvents include ketones, such as acetone, and halogenated solvents such as chloroform. It is desirable that the solvent contain less than about 5% by weight of water. Preferably, the solvent contains less than about 1% by weight of water. Most preferably, the solvent is anhydrous.

The particle mixture and solvent is preferably agitated for a period of time and under conditions sufficient to achieve substantial homogeneity of the mixture. In an exemplary embodiment, the mixture and solvent is tumbled on rollers for about one to about two hours. As used herein, "homogeneity" and "homogeneous" describe a composition that is substantially uniform in structure and/or composition throughout. The agitation may comprise sonication or mechanical vibration, or both. The agitation may further comprise stirring. The term "substantially homogeneous" is to be understood within the context of the invention and is not to be taken as an absolute.

In the present invention, substantially all of the solvent is removed from the mixture. Methods of removing solvent are known in the art per se. In certain embodiments, the solvent can be removed under reduced pressure. In other embodiments, the solvent can be removed by evaporation. The mixture may optionally be re-blended to further ensure homogeneity. For example, the dried powder may be tumbled for about one to about two hours on rollers.

Also in accordance with the present invention, at least one filler may be added to the mixture of polymer and bioactive glass. Such fillers can comprise, at least partially, reinforcing fibers. Examples of preferred fillers include carbon, glass, radiopaque material, barium glass, resorbable material, or mixtures thereof. In certain embodiments, the filler may comprise calcium phosphate having macro-, meso-, and microporosity. More preferably, the porosity of the calcium phosphate is interconnected. The preparation of preferred forms of calcium phosphate for use in the present invention is described in U.S. Pat. Nos. 6,383,519 and 6,521,246, incorporated herein by reference in their entireties. An exemplary calcium phosphate product is Vitoss® Scaffold Synthetic Cancellous Bone Void Filler (Orthovita, Inc., Malvern, Pa.).

In accordance with the present invention, the steps described for preparing the bioactive composite may be repeated to achieve substantial homogeneity of the composite.

Figure 9A:
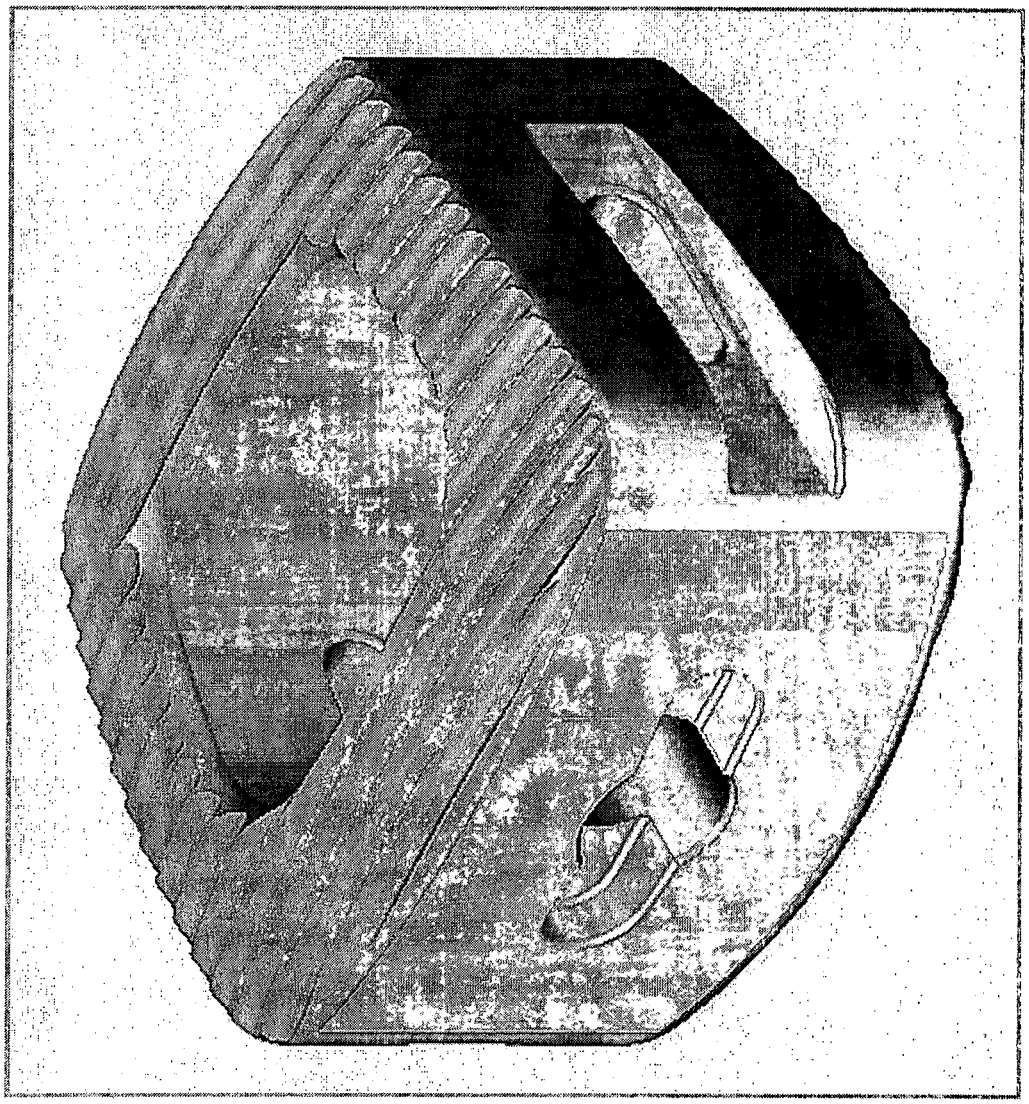
FIG. 9A is an example of one embodiment of a shaped body of the present invention.
Figure 9B:
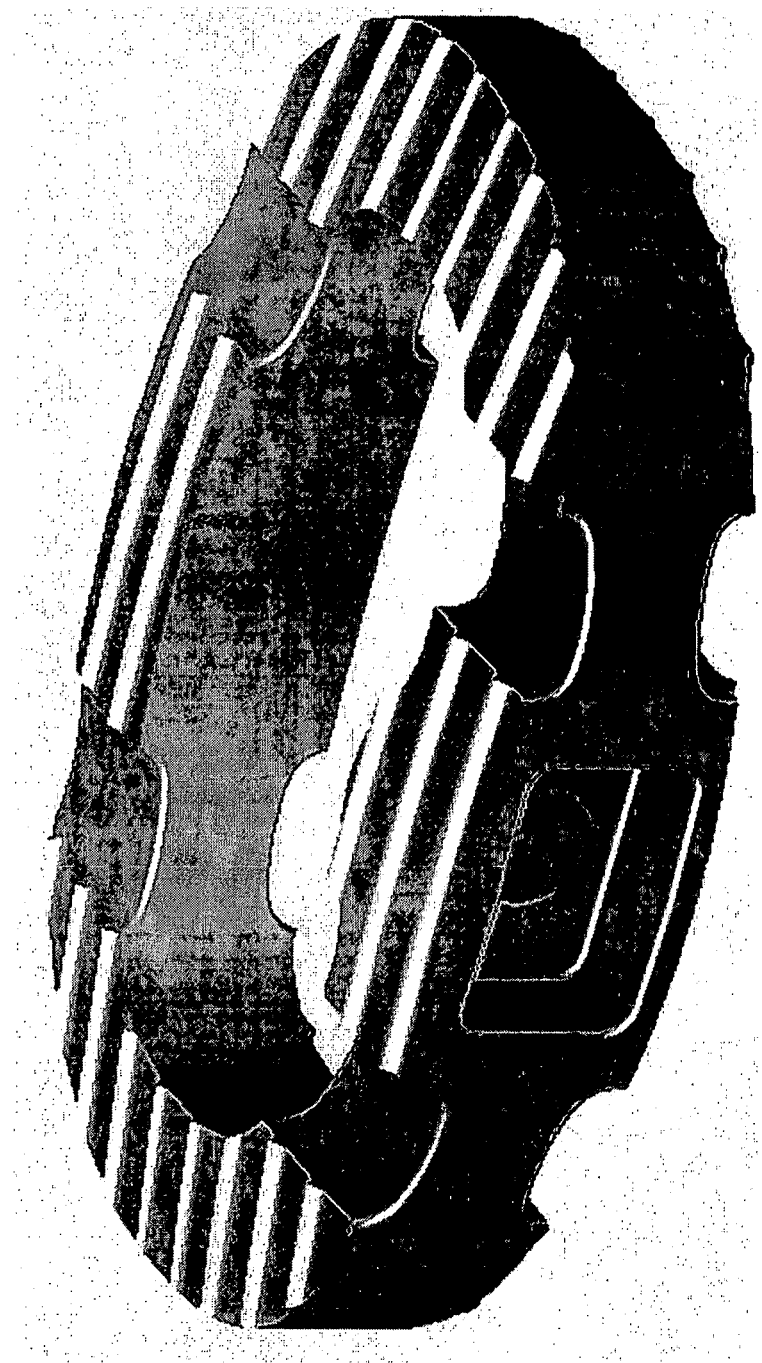
FIG. 9B is an example of one embodiment of a shaped body of the present invention.
Figure 9C:
FIG. 9C is an example of one embodiment of a shaped body of the present invention.
Figure 10C:
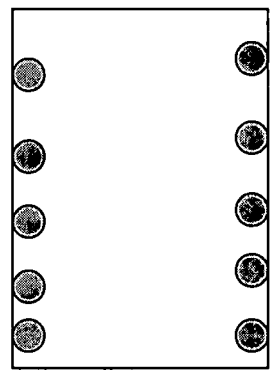
FIGS. 10A-10C illustrate exemplary composite structures of the present invention. Bioactive materials are represented by filled gray circles.
Figure 10B:
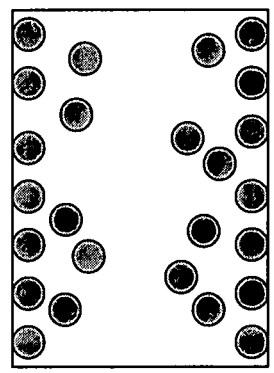
Figure 10A:
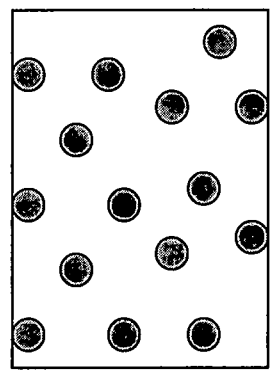

Having prepared the bioactive particle composite according to the methods described herein, the composite can be molded using conventional molding techniques to form an integral shaped bioactive implant body, such as those shown in FIGS. 9A-9C. Alternatively, the composite may be molded such that after further machining, a shaped body for implantation is prepared. For example, the composite may be molded to form a generic shape, for example a cylinder or block, which is then machined to a pre-selected implant shape. A mold can be filled with the composite and pressure, for example about 2 to about 80 MPa, can be applied to form a bioactive implant or a generic shape suitable for further machining. Heat sufficient to melt at least one component of the composite can also be used. In addition to using heat to melt at least one component of the composite, vibrational, radiofrequency, or microwave energy, or combinations thereof, can be used to melt at least one component of the composite.

Once the bioactive spinal implant has been molded, treatment of the implant can be performed to alter the mechanical properties of the composite. For example, after molding, the implant can be held at a temperature above room temperature for a period of time. In other instances, the molded implant can be cooled to room temperature or below by, for example, immersion in water or liquid nitrogen.

Once the composite has been molded into a desired shaped body, conventional finishing techniques may be employed, such as milling, cutting, drilling, and/or sanding of the shaped body.

Composite structures contemplated by the present invention include homogeneous composites prepared by blending PEEK, or a related polymer, with bioactive glass, using the methods described herein. Also within the scope of the present invention are composites comprising a gradient of bioactive material. For example, the gradient can vary along one or more dimensions. In another example, there may be greater concentrations of bioactive material in one or more portions of the composite as compared with other portions. Also envisioned are composites comprising layers of one or more types or concentrations of bioactive material, so long as at least one layer is in accordance with the invention. Structures prepared from such composites may have a bioactive portion of the composite at one or more specific locations, such that the bioactive material occurs where design specifications call for bone bonding. In other embodiments, structures prepared using the composites of the present invention may have bioactive materials adhered to the surface. In further embodiments of the present invention, the structures may be coated with materials described herein and such coatings may be useful on metals, polymeric, or ceramic intracorporeal implants.

Figure 1A:
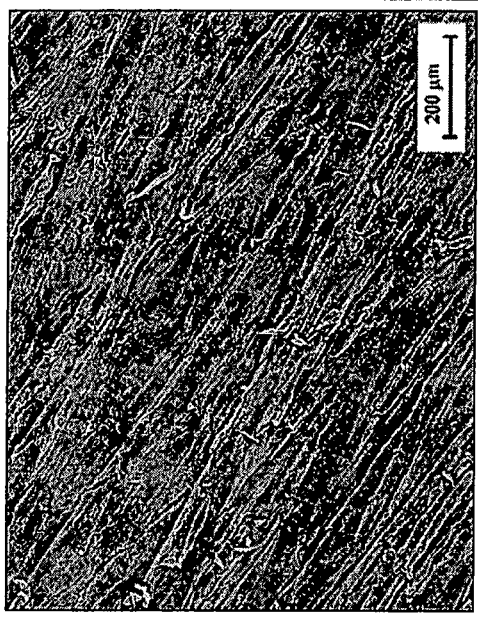
FIG. 1A depicts a SEM (100×) of a sample of PEEK after immersion in simulated body fluid (SBF) for 1 day.
Figure 1C:
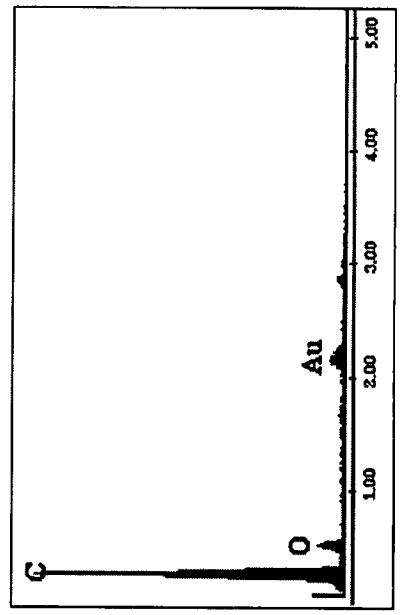
FIG. 1C depicts an energy dispersive spectroscopy (EDS) spectrum of a sample of PEEK after immersion in SBF for 1 day. The spectrum corresponds to the sample region shown in FIG. 2B.
Figure 5B:
FIG. 5B depicts a SEM (1000×) of a sample of PEEK after immersion in SBF for 14 days.
Figure 5A:
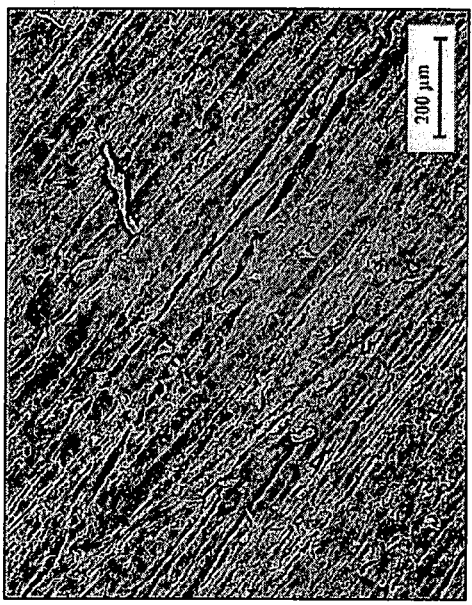
FIG. 5A depicts a SEM (100×) of a sample of PEEK after immersion in simulated body fluid (SBF) for 14 days.
Figure 5C:
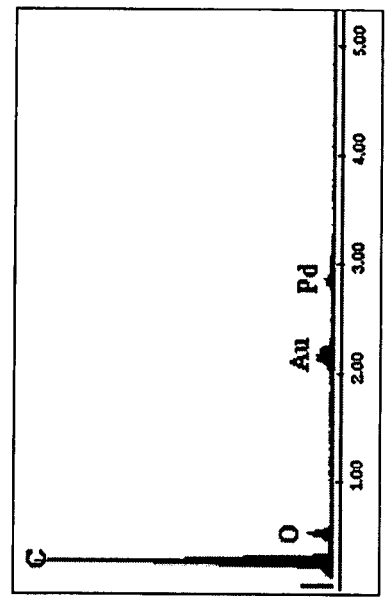
FIG. 5C depicts an EDS spectrum of a sample of PEEK after immersion in SBF for 14 days. The spectrum corresponds to the sample region shown in FIG. 5B.
Figure 6A:
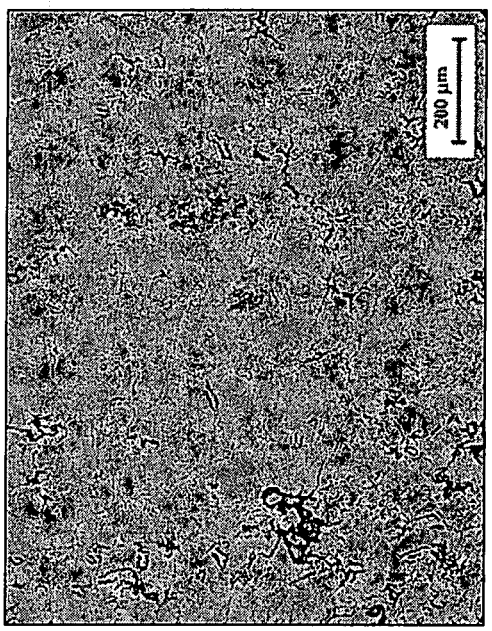
FIG. 6A depicts a SEM (100×) of an exemplary embodiment of the present invention comprising PEEK and combeite glass-ceramic (50% by weight), after immersion in SBF for 14 days.
Figure 6B:
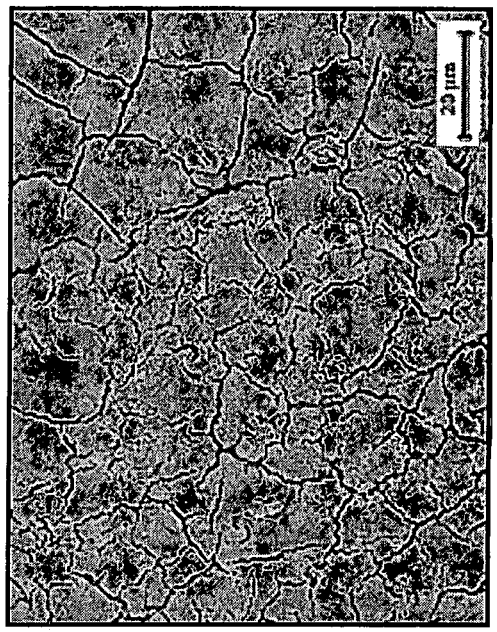
FIG. 6B depicts a SEM (1000×) of an exemplary embodiment of the present invention comprising PEEK and combeite glass-ceramic (50% by weight), after immersion in SBF for 14 days.
Figure 6C:
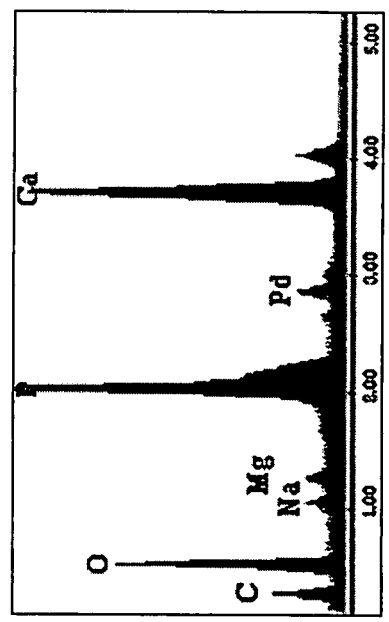
FIG. 6C depicts an EDS spectrum of an exemplary embodiment of the present invention comprising PEEK and combeite glass-ceramic (50% by weight), after immersion in SBF for 14 days. The spectrum corresponds to the sample region shown in FIG. 6B.
Figure 7:
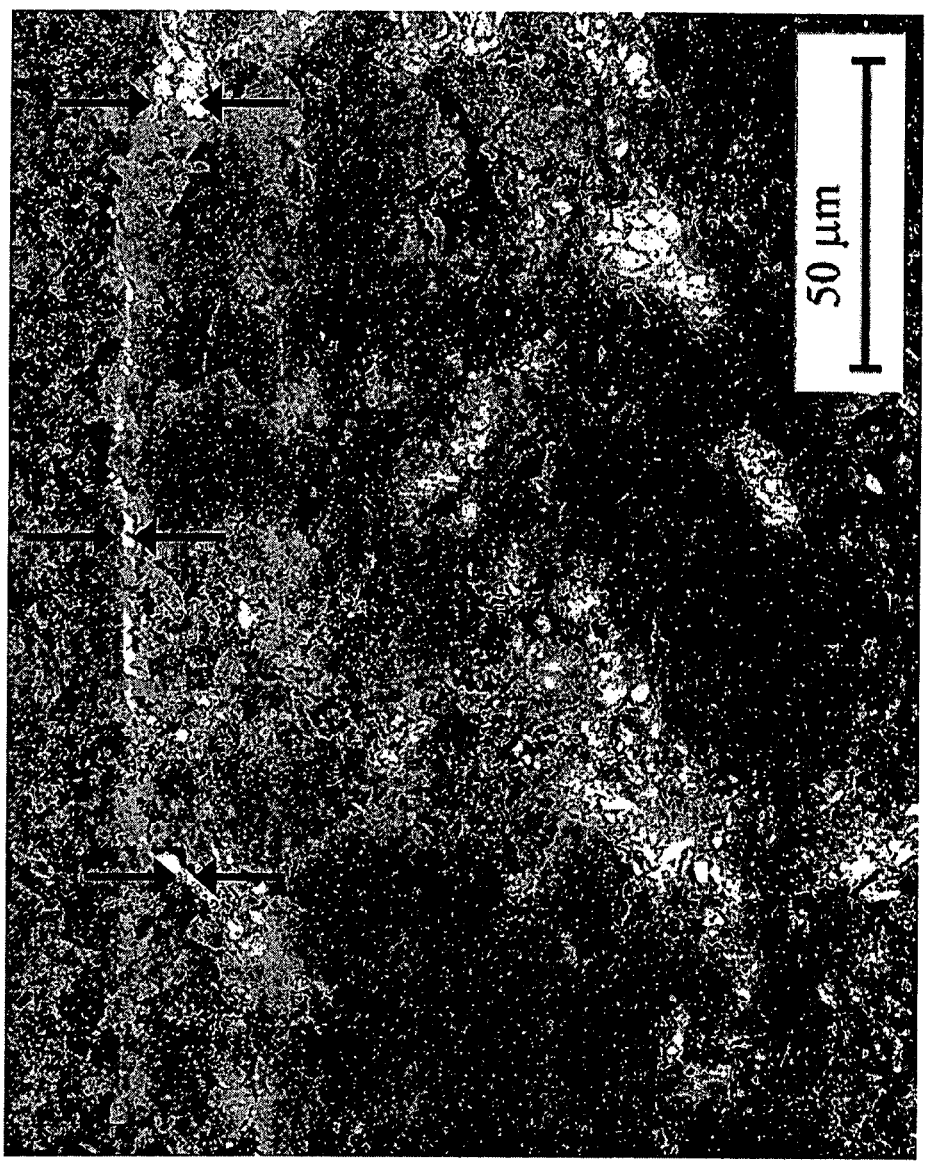
FIG. 7 depicts a SEM of a cross-section of an exemplary embodiment of the present invention comprising PEEK and combeite glass-ceramic (50% by weight), after immersion in SBF for 14 days. The arrows demarcate deposition of calcium phosphate along the surface of the composite.

Composites and shaped bodies of the present invention preferably demonstrate load-bearing and mechanical properties suitable for use in spinal implants. Composites and shaped bodies of the present invention also preferably demonstrate bioactivity. As used herein, "bioactive" relates to the chemical formation of a calcium phosphate layer (amorphous, partially crystalline, or crystalline) via ion exchange between surrounding fluid and the composite material. "Bioactive" also pertains to materials that, when subjected to intracorporeal implantation, elicit a reaction. Such a reaction leads to bone formation, attachment into or adjacent to implants, and/or bone formation or apposition directly to the implants, usually without intervening fibrous tissue. Referring to FIGS. 1-8, a composite, comprising PEEK and 50% by weight of combeite glass-ceramic (having <53 micron average particle size), was prepared using the methods set forth herein. In vitro bioactivity studies were performed with the composites, prepared as described herein, using the method of *Kokubo, How useful is SBF is predicting in vivo bone bioactivity, Biomaterials* (2006) 27:2907-2915. After immersion in simulated body fluid (SBF) for 1 day, the formation of calcium phosphate can be observed (FIGS. 2A-2C). By comparison, a sample of PEEK, without the bioactive component, immersed in SBF for 1 day, does not result in the formation of calcium phosphate (FIGS. 1A-1C). After 7 days of immersion in SBF, increasing amounts of calcium phosphate formation can be observed in the composite (FIGS. 4A-4C), whereas no calcium phosphate formation is observed in the PEEK sample (FIGS. 3A-3C). After 14 days of immersion in SBF, calcium phosphate can still be observed in the composite sample (FIGS. 6A-6C), but no calcium phosphate formation is observed in the PEEK sample (FIGS. 5A-5C). A cross section of a composite sample which had been immersed in SBF is shown in FIG. 7. As denoted by arrows, calcium phosphate formation is observed on the surface of the composite material. The distribution of bioactive glass within the sample can also be appreciated in this view.

FIGS. 8A-8E are fourier transform infrared (FTIR) spectra of composites comprising PEEK and 50% by weight of combeite glass-ceramic, prepared using the methods set forth herein. As can be seen, characteristic peaks for calcium phosphate (1000, 600, and 560 $cm^{-1}$, see FIG. 8F) increase over time, indicative of bioactivity and progression to a mature crystalline hydroxyapatite. Thus, an embodiment of the present invention is a composite comprising PEEK and bioactive glass wherein the composite is bioactive.

The following examples are set forth to further describe the invention and are not intended to be limiting.

Example 1

1500 grams of PEEK powder (GoodFellow Corp., Devon, Pa. nominal 80 micron) and 1500 grams of combeite glass-ceramic (Orthovita, Inc., Malvern, Pa., average particle size<53 micron, non-silanated) were combined in a polyethylene bottle and tumbled on rollers for about 1 to 2 hours. Anhydrous ethanol (2:1, ethanol:powder mixture) was added and the resulting mixture was sonicated in a glass beaker for about 5 minutes while stirring. The excess alcohol was decanted and the mixture was transferred to a glass tray and dried at about 70° C. for about 12 hours. The mixture was then transferred to a polyethylene bottle and tumbled on rollers for about 1 to 2 hours.

Example 2

The material obtained from Example 1 was loaded into a stainless steel mold. A piston was inserted and about 80 MPa of pressure was applied. The mold was heat pressurized to above 340° C. and was held until the material melted. The mold was then held at 270° C. for about 4 hours before being cooled to room temperature. After cooling, the molded article was removed from the mold and milled.

Example 3

The material obtained from Example 1 was loaded into a stainless steel mold. A piston was inserted and about 80 MPa of pressure was applied. The mold was heat pressurized to above 340° C. and was held until the material melted. The mold was then cooled to room temperature and the molded article was removed from the mold and milled.

Those skilled in the art will appreciate that numerous changes and modifications can be made to the many embodiments of the invention and that such changes and modifications can be made without departing from the spirit of the invention. It is therefore intended that the appended claims cover all such equivalent variations as falling within the true spirit and scope of the invention.

What is claimed is:

1. A bioactive composite comprising a substantially homogenous mixture of polyetheretherketone and an alkali containing bioactive glass having osteoproductive properties, wherein the bioactive glass has a particle size range from 1 to 400 microns, and wherein the bioactive glass comprises from 5% to 60% by weight of the composite wherein at least a portion of the surface alkali of the bioactive glass is depleted from about 5 microns to about 10 microns into the bioactive glass such that alkali reactivity with the polyetheretherketone is reduced at the surface of the bioactive composite.

2. The bioactive composite of claim 1, wherein the polyetheretherketone has a particle size range from 1 to 400 microns prior to formation of said composite.

3. The bioactive composite of claim 1, wherein the bioactive glass is combeite having a particle size range from 1 to 200 microns.

4. The bioactive composite of claim 1, wherein the bioactive glass is combeite having a particle size range from about 90 to 150 microns.

5. The bioactive composite of claim 1, wherein the bioactive glass is combeite having a particle size of less than 53 microns.

6. The bioactive composite of claim 1, wherein the bioactive glass comprises from 45% to 55% by weight of the composite.

7. The bioactive composite of claim 1, wherein the composite further comprises a filler.

8. The bioactive composite of claim 7, wherein the filler is at least one selected from the group consisting of a reinforcing fiber, carbon, glass, a radiopaque material, barium glass, a resorbable material.

9. The bioactive composite of claim 7, wherein the filler is a calcium phosphate material.

10. A bioactive composite comprising a substantially homogenous blend of polyetheretherketone and combeite,
    wherein the polyetheretherketone has a particle size range from 1 to 400 microns,
    wherein the combeite having has a particle size range from 1 to 400 microns, and,
    wherein the combeite comprises between about 5% to about 60% by weight of the composite,
    wherein at least a portion of the surface alkali of the bioactive glass is depleted from about 5 microns to about 10 microns into the bioactive glass such that alkali reactivity with the polyetheretherketone is reduced at the surface of the bioactive composite.

11. The bioactive composite of claim 10, wherein the combeite comprises from 20% to 40% by weight of the composite.

12. A shaped body for intracorporeal implantation comprising the bioactive composite of claim 1.

13. A intracorporeal implant comprising the bioactive composite of claim 1.

14. A spinal implant comprising the bioactive composite of claim 1.

15. The bioactive composite of claim 1 prepared from a blend of polyetheretherketone particles and alkali-containing bioactive glass ceramic particles; the blend formed into a particle mixture to which a polar organic solvent has been added to form a weight ratio of solvent to particle mixture of about 1:1 to about 4:1; the mixture having been agitated for a time and under conditions sufficient to achieve substantial homogeneity of the mixture; and substantially all of the solvent having been removed from the particle mixture.

16. A shaped body formed by shaping the bioactive composite of claim 15 under conditions of heat pressurization to melt the bioactive composite.

* * * * *

UNITED STATES PATENT AND TRADEMARK OFFICE
CERTIFICATE OF CORRECTION

Page 1 of 1

PATENT NO.       : 8,968,797 B2
APPLICATION NO.  : 12/442531
DATED            : March 3, 2015
INVENTOR(S)      : James P. Murphy et al.

It is certified that error appears in the above-identified patent and that said Letters Patent is hereby corrected as shown below:

In the claims
Column 9, line 34, "range" should read -- ranging --.
Column 9, line 35, "comprises" should read -- is present in an amount --.
Column 9, line 40, "bioactive composite" should read -- bioactive glass --.
Column 9, line 43, "range" should read -- ranging --.
Column 9, line 45, "range" should read -- ranging --.
Column 9, line 48, "range" should read -- ranging --.
Column 10, line 5, "comprises" should read -- is present in an amount --.
Column 10, line 11, "barium glass," should read -- barium glass, and --.
Column 10, line 17, "range" should read -- ranging --.
Column 10, line 19, "range" should read -- ranging --.
Column 10, line 21, "comprises" should read -- is present in an amount --.
Column 10, lines 23-24, "bioactive glass" should read -- combeite --.
Column 10, line 25, "bioactive glass" should read -- combeite --.
Column 10, line 27, "bioactive composite" should read -- combeite --.

Signed and Sealed this
Third Day of May, 2016

Michelle K. Lee
*Director of the United States Patent and Trademark Office*